United States Patent [19]

Brois et al.

[11] 4,251,232
[45] * Feb. 17, 1981

[54] AMINE DERIVATIVES OF THIO-BIS-LACTONE ACIDS IN COMBINATION WITH COADDITIVE HYDROCARBONS ARE FLOW IMPROVERS FOR MIDDLE DISTILLATE FUEL OILS

[75] Inventors: Stanley J. Brois, Westfield; Antonio Gutierrez, Mercerville; Nicholas Feldman, Woodbridge, all of N.J.

[73] Assignee: Exxon Research & Engineering Co., Florham Park, N.J.

[ * ] Notice: The portion of the term of this patent subsequent to Mar. 6, 1996, has been disclaimed.

[21] Appl. No.: 944,260

[22] Filed: Sep. 21, 1978

Related U.S. Application Data

[63] Continuation-in-part of Ser. No. 875,239, Feb. 6, 1978, Pat. No. 4,142,866.

[51] Int. Cl.$^3$ .............................................. C10L 1/14
[52] U.S. Cl. ...................................... 44/63; 260/343.6
[58] Field of Search ................... 44/63, 80; 260/343.6

[56] References Cited

U.S. PATENT DOCUMENTS

| | | | |
|---|---|---|---|
| 3,600,311 | 8/1971 | Naiman et al. | 44/62 |
| 3,660,058 | 5/1972 | Feldmen et al. | 208/15 |
| 4,062,786 | 12/1977 | Brois et al. | 252/51.5 R |

Primary Examiner—Winston A. Douglas
Assistant Examiner—Y. Harris-Smith
Attorney, Agent, or Firm—R. A. Dexter; J. J. Mahon

[57] ABSTRACT

Amine salts, amic acids, amic acid amine salts bis-amides and imides of oil-soluble thio-bis-($C_{12-50}$ alkyl lactone acid), e.g. a secondary hydrogenated tallow amide of dithio-bis-($C_{16}$-$C_{24}$ alkyl lactone carboxylic acid), are useful in combination with a coadditive hydrocarbon such as an amorphous hydrocarbon or a hydrogenated polybutadiene in improving the cold flow properties of distillate hydrocarbon oils.

13 Claims, No Drawings

AMINE DERIVATIVES OF THIO-BIS-LACTONE ACIDS IN COMBINATION WITH COADDITIVE HYDROCARBONS ARE FLOW IMPROVERS FOR MIDDLE DISTILLATE FUEL OILS

CROSS-REFERENCE TO RELATED APPLICATION

This application is a continuation-in-part of U.S. patent application Ser. No. 875,239, filed Feb. 6, 1978, now U.S. Pat. No. 4,142,866.

BACKGROUND OF THE INVENTION

1. Field of the Invention

The invention relates to amide derivatives of a sulfur compound in combination with a coadditive hydrocarbon as middle distillate fuel flow improvers.

2. Description of the Prior Art

Heating oils and other middle distillate petroleum fuels, e.g., diesel fuels, contain normal paraffin hydrocarbon waxes which, at low temperatures, tend to precipitate in large crystals in such a way as to set up a gel structure which causes the fuel to lose its fluidity thereby presenting difficulties in transporting the fuel through flow lines and pumps. The wax crystals that have come out of solution also tend to plug fuel lines, screens and filters. This problem has been well recognized in the past and various additives known as pour point depressants have been used to change the nature of the crystals that precipitate from the fuel oil, thereby reducing the tendency of the wax crystals to set into a gel.

It is known in the prior art to employ various polymeric and copolymeric materials as pour point depressants for controlling wax deposition of wax-containing petroleum fractions, e.g. U.S. Pat. No. 3,600,311 teaches that branched alkylene polymers having a molecular weight of about 1,000 to 50,000 and with 10–55% branching, e.g. hydrogenated polybutadiene, can be used to improve the cold flow characteristics of middle distillate fuels.

Recently, it has become known that pour point depression alone is not a sufficient phenomenon to alleviate some problems caused by wax crystals in various fuels, especially middle distillates. In those petroleum fractions, it has been observed that the wax crystals formed in the presence of the pour point depressant are often too large to enable the wax-cloudy fuels to pass easily through screens and orifices commonly encountered in the equipment employed either in distribution or in use of such fuels. This problem has been alleviated by the addition to said fraction of petroleum products of wax crystal modifiers which are referred to as flow and filterability improvers.

U.S. Pat. No. 3,961,916 teaches that the low temperature flow characteristics of petroleum middle distillates can be very satisfactorily controlled by the proper choice of a combination of a nucleating agent or wax growth stimulator and a wax crystal growth arrester.

Other additive combinations have been taught for modifying the cold flow characteristics of petroleum fuels including:

U.S. Pat. No. 3,846,093 teaches modifying the low temperature filterability of middle distillate fuels by the addition of an amorphous hydrocarbon and an N-aliphatic hydrocarbyl succinamic acid or derivative thereof; and, U.S. Pat. No. 4,014,663 teaches a synergistic mixture based on the combination of a hydrocarbon which is a derivative of an alphaolefin and said succinamic acid or derivative thereof.

SUMMARY OF THE INVENTION

It has been found that amic acid, amic acid amine salts, bis-amides and imides of thio-bis-($C_{12}$ to $C_{50}$ alkyl lactone carboxylic acid) in combination with a coadditive hydrocarbon of the class consisting of an amorphous hydrocarbon, a hydrogenated butadiene and mixtures thereof further improves the cold flow characteristics of a middle distillate petroleum fuel oil boiling within the range of about 120° C. to about 400° C. at atmospheric pressure.

In accordance with the present invention, a fuel composition is provided which comprises a major proportion, i.e. more than 50% by weight, of a distillate petroleum fraction preferably having an atmospheric boiling range of from about 120° C. to about 400° C. and from about 0.001 to 1.0 wt. % of a flow and filterability improving combination comprising: (a) 1 to 5 parts by weight of an amine derivative, i.e. an amine salt, an amic acid, amic acid amine salt, bis-amide or imide of a thio-bis-($C_{12}$ to $C_{50}$, preferably $C_{16}$ to $C_{24}$, alkyl lactone acid), preferably secondary amine derivatives of the general formula

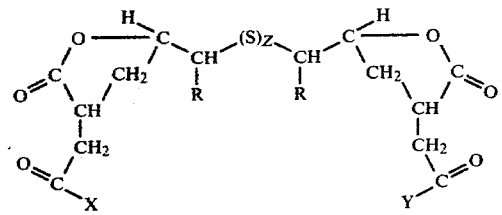

wherein Z represents the number 1 or 2, X can be the same as or different from Y with the proviso that each of X and Y is selected from the following types of substituents consisting of a —OH group, a —OH.$R_1R_2$NH group or a $R_1R_2$N-group and further that (X+Y) represents a

imide group, R represents an alkyl group of from 8 to 40, preferably 12 to 24, $R_1$ and $R_2$ are selected from the class of an aliphatic hydrocarbon of 8 to 30 carbon atoms and an oxyaliphatic hydrocarbon of from 8 to 30 carbon atoms and $R_3$ can be either $R_1$ or $R_2$; and, (b) 1 to 100 parts by weight of a coadditive hydrocarbon of the class consisting of an oil-soluble amorphous hydrocarbon, such as a saturated hydrocarbon fraction, having less than about 5, preferably less than about 1, wt. % of normal paraffin hydrocarbons, which can be illustrated by Coray 200 petrolatum, a hydrogenated polybutadiene having from about 5 to 55, preferably 10 to 30 weight percent 1-2 addition, i.e. branched units and a number average molecular weight ($\overline{M_n}$) ranging from 400 to 10,000, preferably 600 to 3000 and mixtures thereof.

For the amide derivatives the foregoing formula is modified to limit X to the secondary amide group, $R_1R_2$N- and for the cyclic imide said formula is modified to limit X and Y to the imide group

A particularly useful amine derivative for the flow and filterability improving combination is the amine salt of a thio-bis-($C_{12}$ to $C_{50}$, preferably $C_{18}$ to $C_{28}$, alkyl lactone acid), preferably secondary amine salts of the general formula as disclosed in said Ser. No. 875,239, now U.S. Pat. No. 4,142,866.

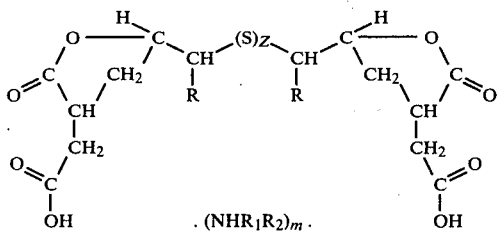

wherein R represents an alkyl group of from 8 to 40, preferably 12 to 24 carbons, Z represents the number 1 or 2, n represents the number of 1 to 2, and $R_1$ and $R_2$ are selected from the class of an aliphatic hydrocarbon of 8 to 30 carbon atoms and an oxyaliphatic hydrocarbon of from 8 to 30 carbon atoms. It is preferred that the weight ratio of a/b is in the range of 4:1 to 1:25, optimally 2:1 to 1:8. All molecular weights herein are measured by Vapor Phase Osmometry (VPO), and Gel Permeation Chromatography (GPC).

Concentrates of 1 to 60 wt. % of said amine derivative additive-hydrocarbon combination in 40 to 99 wt. % of mineral oil, e.g. kerosene, can be prepared for ease of handling.

DETAILED DESCRIPTION OF THE INVENTION

The above flow improver for distillate oils according to this invention is obtained by the reaction of an amine containing 16 to about 60, preferably from about 24 to 48, optimally about 32 carbons, with a thio-bis-($C_{12}$ to $C_{50}$ alkyl lactone carboxylic acid) preferably of the general formula

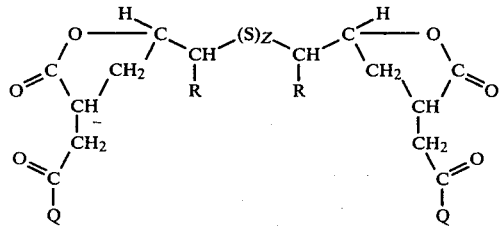

wherein R represents an alkyl group of 5 to 43, preferably 12 to 24 carbons, Z is 1 or 2 and Q depicts an —OH (hydroxyl) group, an —$OR_3$ (lower alkoxy) group where $R_3$ is a $C_1$ to $C_4$ alkyl substituent or

(lower secondary amino) group where $R_4$ and $R_5$ are the same or a different $C_1$ to $C_4$ alkyl, cycloalkyl or heterocyclic substituent.

Illustrative thio-bis-(alkyl lactone acid) coadditive compounds include thio-bis(alkyl substituted lactone carboxylic acid) wherein the alkyl substituent can be pentyl, octyl, dodecyl, tridecyl, n-tetradecyl, pentadecyl, hexadecyl, heptadecyl, nonadecyl, eicosyl, docosyl and branched analogues and mixtures thereof.

Various secondary amines may be used, both those having the same aliphatic and those having different aliphatic hydrocarbon groups containing 8 to 30 carbons. Either alkyl or alkenyl substituents may be present on the nitrogen, each having at least 8, preferably from 14 to 24 carbon atoms. For the primary amines which give imide products the hydrocarbon group contains from 6 to 30, preferably 14 to 24 carbons including both aliphatic and aromatic substituents. For the most part, the aliphatic hydrocarbon groups will be straight chain, i.e. normal with the amino nitrogen bonded either to internal or terminal carbon atoms.

Examples of: secondary amines include di-n-octyl amine, octyl lauryl amine, dodecyl hexadecyl amine, dioctadecyl amine, di-docosyl amine; and primary amines include benzylamine, octyl amine, dodecyl amine, hexadecyl amine, tetracosyl amine.

Amine mixtures may also be used and many amines derived from natural materials are mixtures. Thus, coco amine derived from coconut oil is a mixture of secondary amines with straight chain alkyl groups ranging from $C_8$ to $C_{18}$. Particularly useful is di-tallow secondary amine, derived from hydrogenated tallow, which secondary amine is a mixture of $C_{14}$ to $C_{18}$ straight chain alkyl groups.

The amic acid and amic acid amine salts are readily prepared by mixing together neat from 1 to 2 moles of secondary amine to a molar amount of the thio-bis-(alkyl lactone acid) conveniently as prepared, or in an inert solvent such as xylene. The reagents are usually mixed in xylene and heated for several hours at reflux until sufficient water is azeotroped from the reaction mixture to form the amic acid and the amic acid amine salt products. Thus mild heating from ambient temperature to about 150° C. may facilitate the amic acid and/or amic acid salt formation.

The bis-amide products are readily produced via the condensation of thio-bis-(alkyl lactone acid) with 2 moles of secondary amine at higher temperatures, e.g., 210°–240° C. although temperatures of from 150° C. to 250° C. are useful for this bis-amide.

The thio-bis-(alkyl lactone acid) which is used as the precursor for the amide derivatives may be an individual compound or mixtures of compounds. That is, various alkyl groups of varying branchiness, differing number of carbon atoms or different positions of attachment relative to the lactone acid group may be used. Alternatively, a single isomer may be used. Since mixtures are generally more readily available, to that degree they are preferred. Frequently, mixtures will be used of thio-bis-(alkyl lactone acid) wherein no single homolog and/or isomer is present in amount greater than 25 mole percent.

The thio-bis-(alkyl lactone acid) is readily prepared according to the teachings of U.S. patent application Ser. No. 726,206 filed Sept. 24, 1976, now U.S. Pat. No. 4,062,786 of common assignee, which is incorporated herein by reference thereto. The thio-bis-(lactone acid) can be conveniently prepared by sulfur halide addition to the double bond in alkenyl succinic anhydride at about −60° C. to 100° C. followed by lactonization via an internal displacement of the halide with water. Alternatively, alkenyl succinic acid can be reacted with sulfur halide at from about −60° C. to 100° C. resulting in adduct formation which undergoes lactonization at temperatures above about 50° C. since the temperature governs the displacement of the halide e.g. chloride by a vicinal carboxylic acid group.

The preparation of alkenyl succinic anhydrides and acids is well known by either the "ene" reaction wherein an olefin is reacted with maleic anhydride or fumaric acid or a Diels-Alder reaction of a halogen substituted aliphatic material, e.g. chloro-polyisobutylene, with maleic anhydride or fumaric acid (see U.S. Pat. No. 2,568,876).

If desired, solvents comprising hydrocarbons such as pentane, hexane, heptane, cyclohexane, mineral oil; halocarbons such as methylene chloride, chloroform, carbon tetrachloride, aromatics such as toluene, chlorobenzenes, xylene; ethers such as diethyl ether and tetrahydrofuran (THF); and, acids such as acetic, propionic and trifluoroacetic acid, can be used in favorably controlling viscosity and reaction temperature. The mode of addition of reagents is dictated by convenience. Usually, the sulfur halide, preferably $SCl_2$ or $S_2Cl_2$ is added dropwise to the alkenyl acid or acid anhydride, preferably diluted in an inert diluent.

The anhydride reactants can be the same or different so that mixtures of symmetrical and unsymmetrical thiobis, i.e. bridged, anhydride or acid products can be constructed at will. Higher conversions to unsymmetrical adducts can be achieved by the interaction of equimolar amounts of sulfur halide and one type of alkenedioic acid or anhydride at low temperatures i.e. −60° C. to about 20° C., to generate a discrete 1:1 sulfur halide-alkenyl succinic anhydride or acid adduct exclusively. Subsequent addition of a second type of unsaturated anhydride affords the unsymmetrical bridged product predominantly.

Increasing bridging temperature and branching in the alkenyl anhydrides tend to accelerate the elimination of HCl from the intermediate adducts. Since the unsaturated bridged products can be further reacted with a sulfur halide reagent, it becomes necessary in some cases, to modify the theoretical 2:1 stoichiometry of alkenyl succinic anhydride or acid to sulfur halide to effect complete bridging. Accordingly, at higher temperatures, e.g. 100° C., molar ratios of alkenyl succinic anhydride or acid to sulfur halide in the range of 1.5:1 to 1:1 may be required to realize higher conversions to bridged structures. Thus in summary, the thio-bis-(alkyl lactone carboxylic acid) is obtained from the reaction of from about 1 to 2 moles of alkenyl succinic anhydride or acid per mole of sulfur halide, preferably $S_xCl_2$ wherein x is 1 or 2, at a temperature of from −60° C. to 100° C. followed by lactonization which is obtained with the addition of water for the anhydride and may be synchronous with dehydrohalogenation for the acid reactant when the temperature is above about 50° C.

AMORPHOUS HYDROCARBON

The amorphous hydrocarbon useful in this invention as coadditive with the amine salt is an amorphous, normally solid, essentially saturated hydrocarbon fraction having a number average molecular weight within the range from about 600 to about 3,000, said hydrocarbon fraction being substantially free of normal paraffinic hydrocarbons, preferably having no more than about 1 wt. % of normal paraffins, and having been obtained from a residual petroleum oil. The amorphous hydrocarbon is fully described in U.S. Pat. No. 3,660,058 (see particularly column 2, lines 30 ff) which is incorporated herein by reference thereto.

An amorphous hydrocarbon fraction can be obtained by deasphalting a residual petroleum fraction and then adding a solvent such as propane, lowering the temperature of the solvent-diluted residuum, and recovering the desired solid or semi-solid amorphous product by precipitation, followed by filtration. The residual oil fractions from which the desired amorphous hydrocarbons are obtained will have viscosities of at least 125 SUS at 99° C. Most of these residual oils are commonly referred to as bright stocks.

HYDROGENATED POLYBUTADIENE

Useful hydrogenated polybutadienes are described in U.S. Pat. No. 3,600,311. Hydrogenated polybutadienes are branched polymers which have about 5 to 55, preferably 10 to 30, 1-2 addition and 45 to 95, preferably 70 to 90, 1-4 addition and usefully have a number average molecular weight ($\overline{M_n}$) of 400 to 10,000, are readily prepared by polymerizing butadiene in a suitable solvent, e.g. hydrocarbon, in the presence of an organometallic catalyst, e.g. n-butyl lithium. The resulting polymer is then hydrogenated e.g. with hydrogen in the presence of a nickel catalyst until saturated, e.g. 1 wt. % unsaturation.

MIDDLE DISTILLATE FUELS

The distillate fuel oils that can be improved by this invention include those having boiling ranges within the limits of about 120° to about 400° C. The distillate fuel oil can comprise straight run or virgin gas or cracked gas oil or a blend in any proportion of straight run and thermally and/or catalytically cracked distillates.

The most common petroleum middle distillate fuels are kerosene, diesel fuels, jet fuels and heating oils. Since jet fuels are normally refined to very low pour points there will be generally no need to apply the present invention to such fuels. The low temperature flow problem is most usually encountered with diesel fuels and with heating oils. A representative heating oil specification calls for a 10 percent distillation point no higher than about 226° C., a 50 percent point no higher than about 272° C., and a 90 percent point of at least 282° C. and no higher than about 338° C., to 343° C., although some specifications set the 90 percent point as high as 357° C. Heating oils are preferably made of a blend of virgin distillate, e.g., gas oil, naphtha, etc., and cracked distillates, e.g., catalytic cycle stock. A representative specifications for a diesel fuel includes a minimum flash point of 38° C. and a 90 percent distillation point between 282° C. and 338° C. (See ASTM Designations D-396 and D-975).

The additive combination of the invention may be used alone or in combination with still other fuel additives; e.g., corrosion inhibitors; antioxidants, sludge inhibitors, etc.

The invention will be further understood by reference to the following examples which include preferred embodiments of the invention.

EXAMPLES

The following materials were used:

BIS-AMINE SALT OF THIO-BIS-(ALKYL LACTONE ACID)

This is the bis, hydrogenated, di-tallow amine salt of dithio-bis (alkyl lactone carboxylic acid) prepared via the steps of: (1) forming an adduct of $S_2Cl_2$ and $n-C_{18}$ succinic acid which upon heating to 50°–100° C., underwent dehydrohalogenation and lactonization; and (2) reacting the product from about twice the molar amount of the hydrogenated di-tallow amine which provides a product designated hereafter as the Bis-Amine Salt.

Two hundred grams (~0.54 mole) of n-octadecenyl succinic acid were dissolved in a liter of $CHCl_3$ and 36.7 g (0.272 mole) of sulfur monochloride ($S_2Cl_2$) were added dropwise to the stirred solution at room temperature. The exothermic process was accompanied by vigorous HCl evolution. After refluxing the mixture for about eight hours, the solution was cooled and solids separated. Filtration gave 19 g of solid (m.p. 131°–136° C.) which featured an IR spectrum with intense carbonyl bands at 5.62 and 5.72 microns, and analyzed for 66.42% C., 9.63% H, and 8.22% S. Theory for the adduct ($C_{44}H_{78}O_8S_2$) requires 66.12% C, 9.84% H, and 8.02% S. Rotoevaporation of the supernatant gave a solid product in high yield. The proposed structure (I) for dithio-bis-(alkyl lactone acid) namely 6,6'-dithio-bis-(3,5-carbolactone-1-heneicosanoic acid), is given hereafter:

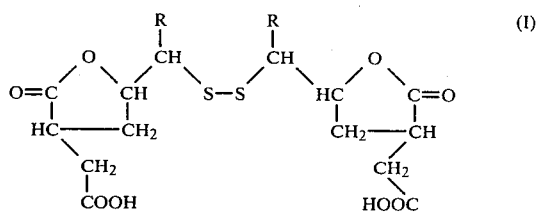

wherein R represents $n-C_{15}H_{31}$.

The Bis-Amine Salt is prepared as follows:

Eight grams (~0.01 mole) of the thio-bis (alkyl lactone acid) as prepared above was dissolved in 25 ml of tetrahydrofuran (THF) and combined with 10.2 g (0.02 mole) of hydrogenated di-tallow amine purchased as Armeen 2HT from Armak Corp. of Chicago, IL. The mixture was allowed to reflux i.e. about 60° C. for a few minutes to assure complete reaction.

While the reaction solution was still hot, acetone was added to the cloud point and a white solid precipitated out while cooling to room temperature. The solid was filtered, collected and dried at room temperature. Quantitative yield of the thio-bis (alkyl lactone acid) salt was obtained. The infrared spectrum of the Bis-Amino Salt of (I) shows the characteristic bands for the lactone acid salt of 5.6 microns for the lactone carboxyl and 6.3–6.4 microns for the carboxylate carbonyl functionality.

MONO AMINE SALT OF THIO-BIS (ALKYL LACTONE ACID)

The thio-bis (alkyl lactone acid) salt containing only one equivalent of said di-tallow amine was prepared in a similar manner as above, except that 0.01 mole of said thio-bis (alkyl lactone acid) as shown in (I) was treated with 0.01 mole of said di-tallow amine.

AMIC ACID AND AMIC ACID AMINE SALT OF DITHIO-BIS-(ALKYL LACTONE ACID)

(a) The amic acid amine salt of dithio-bis-(alkyl lactone acid) (I) is readily obtained along with the amic acid of dithio-bis-(alkyl lactone acid) (I) when one takes the procedure of preparing the bis amine salt and changes it only by heating the reactants at a higher temperature, e.g. this can be done by heating said reactants in 4 parts of xylene [one mole of dithio-bis-(alkyl lactone acid) to two moles of said hydrogenated di-tllow amine] at reflux of about 140° C. for six hours. Water is azeotroped from the reaction mixture to form the amic acid and amic acid amine salt products. Cooling the reaction mixture to ambient temperature afforded a solid product which corresponded to the amic acid amine salt, i.e. di-tallow amine salt of the di-tallow monoamide of dithio-bis-(alkyl lactone acid).

(b) A second product crystallized from the mother liquor obtained for filtration of the crystals of the amic acid amine salt upon slight cooling and standing which corresponds to the amic acid, i.e. the di-tallow monoamide of dithio-bis-(alkyl lactone acid).

BIS-AMIDE OF THIO-BIS-(ALKYL LACTONE ACID)

The bis-amide products are readily produced via the condensation of process (a) availed of for preparation of the amic acid amine salt product except that the condensation is at a higher temperature, e.g. from 210°–240° C., and a period of 2 hours. Infrared analysis showed the presence of a lactone amide product believed to be the bis-(di-tallow amide) of dithio-bis-(alkyl lactone acid) (I).

IMIDE OF THIO-BIS-(ALKYL LACTONE ACID)

Twenty (20)g (ca. 0.025 mole) of the dithio-bis-(pentadecyl lactone acid) were dissolved in 100 ml of xylene and combined with 6.7g (ca. 0.025 mole) of the hydrogenated tallow amine (HT) purchased an Armeen HT from Armak Corp. of Chicago, IL. The mixture was heated to azeotrope the water of reaction for about 1½hours.

The xylene was rotoevaporated under high vacuum at 100° C. until constant weight, obtaining an oil residue. A quantitative yield of the dithio-bis-alkyl lactone imide was obtained. The infrared spectrum showed the characteristic bands for the lactone and imide absorption, i.e. 5.6 microns for the lactone and 5.9 microns for the cyclic imide Elemental analysis showed 1.31 wt. % of nitrogen (theory was 1.36).

For imide preparation equimolar amounts of the thio-bis-(alkyl lactone acid) and the primary amine, i.e. ($C_6-C_{30}$ hydrocarbyl) $NH_2$, are reacted (neat or in a solvent such as xylene) at from 140° C. to 250° C., preferably 160° C. to 220° C., until completion as evidenced by cessation of water evolution and/or maximal imide absorption at 5.9 microns based on infrared analysis.

HYDROGENATED POLYBUTADIENE

The hydrogenated polybutadiene had an $(\overline{M_n})$ of about 1250, a Bromine No. of 0.3 and a Fisher-Johnes melting point of 33°–44° C. The hydrogenated polybutadiene was prepared with a n-butyl lithium catalyst and hydrogenated with hydrogen in the presence of a Raney nickel catalyst.

AMORPHOUS HYDROCARBON

An amorphous hydrocarbon fraction (m.p. 43.9 g.) obtained by propane precipitation from the deasphalted residuum of a Texas coastal crude oil was found by mass spectrographic analysis, and by gas chromatography, to contain 5 wt. % of isoparaffins, 22 wt. % of aromatic hydrocarbons, 73% of cycloparaffins, and no more than a trace of normal paraffin hydrocarbons. The number average molecular weight of this material was about 775 as determined by osmometry.

The distillation characteristics of this solid hydrocarbon fraction were as follows:

TABLE I

| Distillation (ASTM D-1160) | Vapor Temp. at 5 mm Hg | Vapor Temp. Converted to Atmospheric Pressure |
|---|---|---|
| Initial BP | 228° C. | 401° C. |
| 5% | 310° C. | 497° C. |
| 10% | 336° C. | 526° C. |
| 20% | 364° C. | 557° C. |
| 24% | 365° C. | 558° C. |

Only 24% would distill over.
There were 75% bottoms and 1% loss.

FUEL

The properties of the middle distillate fuels tested are summarized in Table II which follows:

TABLE II

|  | Fuel 1 | Fuel 2 | Fuel 3 |
|---|---|---|---|
| Cloud Point, °C. | −1 | +1 | 0 |
| Distillation, °C. (per ASTM D-86) | | | |
| IBP | 162 | 170 | 172 |
| 20% | 220 | 225 | — |
| 95% | 346 | 343 | — |
| FBP | 370 | 371 | 370 |
| n-Paraffin Range, Carbon Nos. | 10–29 | 11–29 | 11–30 |

Blending of the additives into the fuel was accomplished by their dissolution into the fuel oil. This was done while warming, e.g. heating the oil and additive to about 90° C. if the additive or mixture of additives per se were added, and stirring.

The blends were then tested for their cold flow properties in the test described below.

THE COLD FILTER PLUGGING POINT TEST (CFPPT)

The cold flow properties of the blend were determined by the Cold Filter Plugging Point Test (CFPPT). This test is carried out by the procedure described in detail in "Journal of the Institute of Petroleum," Volume 52, Number 510, June 1966 pp. 173–185. In brief, a 40 ml. sample of the oil to be tested is cooled by a bath maintained at about −34° C. Periodically, (at each one degree Centrigrade drop in temperature starting from 2° C. above the cloud point) the cooled oil is tested for its ability to flow through a fine screen in a time period. This cold property is tested with a device consisting of a pipette to whose lower end is attached an inverted funnel positioned below the surface of the oil to be tested. Stretched across the mouth of the funnel is a 350 mesh screen having an area of about 0.45 square inch. The periodic tests are each initiated by applying a vacuum to the upper end of the pipette whereby oil is drawn through the screen up into the pipette to a mark indicating 20 ml. of oil. The test is repeated with each one degree drop in temperature until the oil fails to fill the pipette within 60 seconds. The results of the test are reported as the temperature in °C. at which each of the oils fail to fill the pipette in the prescribed time.

The blends prepared and the test results are summarized in Table III which follows:

TABLE III

Effectiveness of Additives in the Fuels

| Example | Wt. % Active Ingredient | Additive | Fuel 1 CFPPT °C. | Fuel 2 CFPPT °C. | Fuel 3 CFPPT °C. |
|---|---|---|---|---|---|
| 1 | — | none | 0° C. | | |
| 2 | 0.07 | Amorphous Hydrocarbon | −6 | | |
| 3 | 0.07 | Bis-Amine Salt | −2 | | |
| 4 | { 0.05 / 0.01 | Amorphous Hydrocarbon / Bis-Amine Salt | −8 | | |
| 5 | { 0.05 / 0.02 | Amorphous Hydrocarbon / Bis-Amine Salt | −11 | | |
| 6 | — | none | | 0 | |
| 7 | 0.06 | Hydrogenated Polybutadiene | | −3 | |
| 8 | 0.06 | Bis-Amine Salt | | −1 | |
| 9 | { 0.04 / 0.02 | Hydrogenated Polybutadiene / Bis-Amine Salt | | −8 | |
| 10 | | none | | | −1 |
| 11 | 0.07 | Amorphous Hydrocarbon | | | −6 |
| 12 | 0.06 | Hydrogenated Polybutadiene | | | −5 |
| 13 | 0.04 | Amic Acid Amine Salt | | | −4 |
| 14 | 0.04 | Amic Acid | | | −3 |
| 15 | 0.04 | Bis-Amide | | | −3 |
| 16 | { 0.05 / 0.02 | Amorphous Hydrocarbon / Amic Acid Amine Salt | | | −14 |

TABLE III-continued

| Example | Wt. % Active Ingredient | Additive | Fuel 1 CFPPT °C. | Fuel 2 CFPPT °C. | Fuel 3 CFPPT °C. |
| --- | --- | --- | --- | --- | --- |
| 17 | 0.05 / 0.02 | Amorphous Hydrocarbon / Amic Acid | | | −11 |
| 18 | 0.05 / 0.02 | Amorphous Hydrocarbon / Bis-Amide | | | −10 |
| 19 | 0.04 / 0.02 | Hydrogenated Polybutadiene / Amic Acid Amine Salt | | | −15 |
| 20 | 0.04 / 0.02 | Hydrogenated Polybutadiene / Amic Acid | | | −11 |
| 21 | 0.04 / 0.02 | Hydrogenated Polybutadiene / Bis-Amide | | | −11 |

The data of Table III clearly demonstrates the synergistic advantage of the coadditive combinations of the invention with comparison of: Examples 2 and 3 with a CFPPT° C. of −6 and −2 respectively, the Example 5 where the coadditive combination reduced the CFPPT° C. down to −11; the single components of Examples 7 and 8 with a CFPPT° C. of −3 and −1 respectively, and Example 9 where the coadditive combination of the invention reduced the CFPPT° C. down to −8° C.; the single components of Examples 1 and 13 with a CFPPT° C. of −6° C. and −4° C. respectively, and Example 16 where a comparable weight of the coadditive combination of the invention reduced the CFPPT° C. down to −14° C.; and, finally another grouping dramatically showing synergism is seen from the single components of Examples 12 and 13 with a CFPPT° C. of −5° C. and −4° C., respectively yet together in Example 19 the coadditive combination gives a CFPPT° C. of −15° C.

It is believed that tertiary amines, e.g. trioctyl amine, tri-dodecyl amine, tri-octadecyl amine and methyl di-octadecyl amine, are suitable to form mono- and bis salts of the thio-bis-(alkyl lactone acid) for subsequent incorporation into middle distillate fuels alone or in combination with said hydrocarbons according to this invention to improve said fuels cold flow properties when present in amounts as described in the foregoing.

The invention in its broader aspect is not limited to the specific details shown and described and departures may be made from such details without departing from the principles of the invention and without sacrificing its chief advantages.

What is claimed is:

1. A fuel composition comprising a major proportion of a distillate petroleum fraction having an atmospheric boiling range of from about 120° C. to about 400° C. and from about 0.01 to 1.0 wt. % of a flow and filterability improving combination comprising: (a) 1 to 5 parts by weight of an amine derivative of thio-bis-($C_{12}$ to $C_{50}$ alkyl lactone carboxylic acid); and (b) 1 to 100 parts by weight of a coadditive hydrocarbon of the class consisting of an oil-soluble amorphous hydrocarbon having less than about 5 wt. % of normal parafin hydrocarbons, a hydrogenated polybutadiene having a number average molecular weight ranging from 400 to 10,000 and mixtures thereof.

2. A fuel composition according to claim 1 wherein said amine derivative is of the general formula

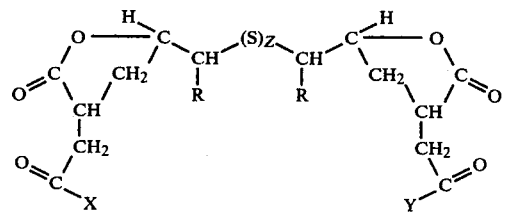

wherein Z represents the number 1 to 2, X can be the same as or different from Y with the proviso that each of X and Y is selected from the following types of substituents consisting of a —OH group, a —OH. $R_1R_2NH$ group or a $R_1R_2N$-group and further that (X+Y) represents a

imide group, R represents an alkyl group of from 8 to 40 carbons, $R_1$ and $R_2$ are selected from the class of an aliphatic hydrocarbon of 8 to 30 carbon atoms and an oxyaliphatic hydrocarbon of from 8 to 30 carbon atoms and $R_3$ can be either $R_1$ or $R_2$.

3. A fuel composition according to claim 2 wherein X is a secondary amide group —$NR_1R_2$.

4. A fuel composition according to claim 1 wherein the weight ratio of said (a) to said (b) ranges from 4:1 to 1:25 and said secondary amine derivative is an amine salt of the general formula:

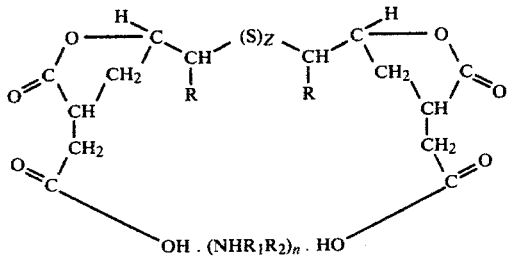

wherein R represents an alkyl group of from 12 to 24 carbons, n represents an integer 1 or 2, Z represents the number 1 or 2, and $R_1$ and $R_2$ are selected from the class of an aliphatic hydrocarbon of 8 to 40 carbon atoms and an oxyaliphatic hydrocarbon of from 8 to 30 carbon atoms.

5. The composition of claim 4 wherein said alkyl group is a substantially linear chain of 15 carbons, $R_1$ and $R_2$ are each a mixture of $C_{14}$ to $C_{18}$ alkyl groups obtained from hydrogenated tallow and n is 2.

6. The composition of claim 2 wherein said hydrocarbon is hydrogenated polybutadiene having a $(\overline{M_n})$ ranging from 600 to 3,000.

7. The composition of claim 2 wherein said hydrocarbon is hydrogenated polybutadiene having a $(\overline{M_n})$ ranging from 600 to 3,000 and said weight ratio of (a) to (b) ranges from 4:1 to 1:25.

8. An additive concentrate comprising from about 1 to 60wt. % of an additive combination consisting essentially of from 1 to 5 parts by weight of an amine derivative of thio-bis-($C_{12}$ to $C_{50}$ alkyl lactone carboxylic acid) and from 1 to 100 parts by weight of an oil-soluble amorphous hydrocarbon having less than about 5 wt. % of normal paraffin hydrocarbons dissolved in a hydrocarbon solvent.

9. An amine derivative according to claim 2 wherein X represents the number 2 and R represents an alkyl group of 12 to 24 carbons.

10. Bis-(di-tallow imide) of dithio-bis-(pentadecyl lactone acid).

11. A fuel composition comprising a major proportion of a distillate petroleum fraction having an atmospheric boiling range of from about 120° C. to about 400° C. and from about 0.01 to 1.0 wt. % of a flow and filterability improving combination comprising: (a) 1 to 5 parts by weight of the amic acid of thio-bis-($C_{12}$ to $C_{50}$ alkyl lactone carboxylic acid); and (b) 1 to 100 parts by weight of a coadditive hydrocarbon of the class consisting of an oil-soluble amorphous hydrocarbon having less than about 5 wt. % of normal paraffin hydrocarbons, a hydrogenated polybutadiene having a number average molecular weight ranging from 400 to 10,000 and mixtures thereof.

12. A fuel composition comprising a major proportion of a distillate petroleum fraction having an atmospheric boiling range of from about 120° C. to about 400° C. and from about 0.01 to 1.0 wt. % of a flow and filterability improving combination comprising: (a) 1 to 5 parts by weight of the amic acid amine salt of thio-bis-($C_{12}$ to $C_{50}$ alkyl lactone carboxylic acid); and (b) 1 to 100 parts by weight of a coadditive hydrocarbon of the class consisting of an oil-soluble amorphous hydrocarbon having less than about 5 wt. % of normal paraffin hydrocarbons, a hydrogenated polybutadiene having a number average molecular weight ranging from 400 to 10,000 and mixtures thereof.

13. A fuel composition comprising a major proportion of a distillate petroleum fraction having an atmospheric boiling range of from about 120° C. to about 400° C. and from about 0.01 to 1.0 wt. % of a flow and filterability improving combination comprising: (a) 1 to 5 parts by weight of the bis-amide of thio-bis-($C_{12}$ to $C_{50}$ alkyl lactone carboxylic acid; and (b) 1 to 100 parts by weight of a coadditive hydrocarbon of the class consisting of an oil-soluble amorphous hydrocarbon having less than about 5 wt. % of normal paraffin hydrocarbons, a hydrogenated polybutadiene having a number average molecular weight ranging from 400 to 10,000 and mixtures thereof.

* * * * *